United States Patent [19]

Takata et al.

[11] Patent Number: 6,066,752
[45] Date of Patent: May 23, 2000

[54] PROCESS FOR PRODUCING SULFUR-CONTAINING ORGANOSILICON COMPOUNDS AND SYNTHETIC INTERMEDIATES THEREOF

[75] Inventors: Toshikazu Takata, Osaka; Motoki Kitagawa; Masato Tabuchi, both of Hyogo; Nobuo Yamada, Tokyo, all of Japan

[73] Assignee: Daiso Co., Ltd., Osaka, Japan

[21] Appl. No.: 09/288,782

[22] Filed: Apr. 9, 1999

[30] Foreign Application Priority Data

Apr. 10, 1998 [JP] Japan .................................. 10-098633
Jul. 27, 1998 [JP] Japan .................................. 10-211124

[51] Int. Cl.$^7$ ........................................................ C07F 7/08
[52] U.S. Cl. ........................................ 556/427; 423/566.2
[58] Field of Search .......................... 423/566.2; 556/427

[56] References Cited

U.S. PATENT DOCUMENTS

| | | | |
|---|---|---|---|
| 4,125,552 | 11/1978 | Speier | 260/448.8 R |
| 4,129,585 | 12/1978 | Buder et al. | 260/448.8 R |
| 4,507,490 | 3/1985 | Panster et al. | 556/427 |
| 5,039,506 | 8/1991 | Bittner et al. | 423/565 |
| 5,466,848 | 11/1995 | Childress | 556/427 |
| 5,468,893 | 11/1995 | Parker et al. | 556/427 |
| 5,489,701 | 2/1996 | Childress et al. | 556/427 |
| 5,583,245 | 12/1996 | Parker et al. | 556/427 |
| 5,596,116 | 1/1997 | Childress et al. | 556/427 |
| 5,663,396 | 9/1997 | Musleve et al. | 556/427 |

FOREIGN PATENT DOCUMENTS

| | | |
|---|---|---|
| 0 361 998 A1 | 4/1990 | European Pat. Off. . |
| 21 41 159 C3 | 3/1973 | Germany . |
| 21 41 160 C3 | 3/1973 | Germany . |
| 22 12 239 C3 | 10/1973 | Germany . |
| 57-26671 | 6/1982 | Japan . |
| 59-12117 | 3/1984 | Japan . |
| 4-63879 | 10/1992 | Japan . |
| 7-228588 | 8/1995 | Japan . |
| 1 394 135 | 5/1975 | United Kingdom . |

OTHER PUBLICATIONS

"Sodium Hydrosulphide" *Inorganic and Theoretical Chemistry*, vol. II (1961), pp. 991.
*Andew. Chem. Int. Ed. Engl.*, vol. 25, (1986), pp. 239.
*Inorganic and theoretical Chemistry*, (1961) vol. II, pp. 981.

*Primary Examiner*—Paul F. Shaver
*Attorney, Agent, or Firm*—Armstrong, Westerman, Hattori, McLeland & Naughton

[57] ABSTRACT

An object of the present invention is to provide a method of obtaining high-purity sulfur-containing organosilicon compounds having polysulfide structure in a simple manner without treatment at high temperatures or under vacuum.

According to the present invention, sulfur-containing organosilicon compounds represented by the formula $(R^1—O)_3—Si—R^2—S_x—R^2—Si—(O—R^1)_3$ is obtained by reacting sulfur, an alkali metal and halogenoalkoxysilane represented by the formula $(R^1—O)_3—Si—R^2—X$ (wherein $R^1$ is a monovalent $C_{1-5}$ hydrocarbon, $R^2$ is a divalent $C_{1-9}$ hydrocarbon, X is a halogen, and x is an integral number of 1 to 8).

15 Claims, No Drawings

PROCESS FOR PRODUCING SULFUR-CONTAINING ORGANOSILICON COMPOUNDS AND SYNTHETIC INTERMEDIATES THEREOF

BACKGROUND OF THE INVENTION

The present invention relates to a novel process for producing sulfur-containing organosilicon compounds which are useftil as additives for rubber. The present invention also relates to a novel process for producing anhydrous alkali sulfides which are useful as synthetic intermediates of the above-mentioned sulfur-containing organosilicon compounds. The sulfur-containing organosilicon compounds are substances which bind synthetic rubber or natural rubber having unsaturated bonds to a filler such as silica, carbon black or surface-reformed carbon black blended into the rubber.

Sulfur-containing organosilicon compounds are industrially useful compounds which have been known from olden times, and many processes for producing them have been known so far.

As a representative process, there is a process wherein halogeno organic silane represented by the following general formula [III] is allowed to react with sodium tetrasulfide, etc. in a solvent at 70° to 80° C. for several hours to give sulfur-containing organosilicon compounds represented by the following general formula [IV].

$$(R^1\text{—O})_3\text{—Si—}R^2\text{—X} \quad \text{[III]}$$

$$(R^1\text{—O})_3\text{—Si—}R^2\text{—S}_x\text{—}R^2\text{—Si—}(O\text{—}R^1)_3 \quad \text{[IV]}$$

(In each formula, $R^1$ is a lower alkyl group, a lower aralkyl group, a lower cycloalkyl group, a lower aryl group, a lower alkoxy group, a lower cycloalkoxy group, an aryloxy group, etc., $R^2$ is a lower alkylene group, X is a halogen atom, and x is an integral number of 2 to 6.)

Examples of known processes are a process wherein the halogeno organic silane [III] is allowed to react with sodium polysulfide such as sodium tetrasulfide to give the sulfiur-containing organosilicon compound [IV] (German Patent Publication Nos. 2,141,159 and 2,212,239), a process wherein the halogeno organic silane [III] is allowed to react with sodium hydrosulfide and sulfur to give the sulfur-containing organosilicon compound [IV] (Japanese Patent Publication Nos. 26671/1982 and 63879/1992), a process wherein the halogeno organic silane [III] is allowed to react with anhydrous sodium sulfide and sulfur to give the sulfur-containing organosilicon compound [IV] (Japanese Laid-open Patent Publication No. 228588/1995), etc.

Both the above-mentioned halogeno organic silane [III], which is the starting material, and the sulfur-containing organosilicon compound [IV], which is the object substance, are liable to be hydrolyzed in the presence of moisture. Accordingly, it is necessary to control moisture carefully during the reactions in order to obtain the object substance in good yields.

Since sodium polysulfide such as sodium tetrasulfide which is used as the raw material in the above-mentioned prior art, and sodium tetrasulfide which is produced by combination of sodium hydrosulfide or sodium sulfide and sulfur (Inorganic and Theoretical Chemistry Vol. II, Longmans Green and Co., Ltd., (1961), p991) have high water absorption properties, it is not easy to obtain anhydrides thereof. A complex drying step is necessary in order to dehydrate these substances, which lowers the yield of the object substance.

As a process wherein anhydrous sodium polysulfide is not used, U.S. Pat. No. 5,596,116 discloses a process wherein sodium ethylate is allowed to react with sulfur, or metallic sodium is allowed to react with sulfur dispersed into ethanol, and then halogenoalkoxysilane is allowed to react with the reaction products. In this process, however, the yields of the object substances are unclear. If sodium ethylate reacts with sulfur, it is unclear what this ethoxide reacts with and even whether or not the ethoxide reacts. U.S. Pat. No. 5,663,396 discloses a process wherein caustic soda is allowed to react with sulfur in a saturated sodium chloride solution, and halogenoalkoxysilane and a phase-transfer catalyst are added to the product in toluene to give sulfur-containing organosilicon compounds. However, this process is accompanied by many side reactions, and yields are low.

There is a process wherein the same procedure as in the above-mentioned process is performed using ammonia instead of sodium as the alkali source. However, a complex step is necessary since hydrogen sulfide and ammonia gas, which are toxic, are used (Japanese Patent Publication No. 12117/1984).

As a process wherein the halogenoalkoxysilane [III] is not used, there is a process wherein alkoxymercaptosilane represented by the following general formula [V] and sulfur chloride or sulfur are used (German Patent Publication No. 2,141,160 and Japanese Patent Publication No. 26671/1982). A method to obtain the alkoxymercaptosilane [V] in a usual manner is known, wherein alkoxychlorosilane is allowed to react with hydrogen sulfide and an alkali metal or an ammonium salt and thiourea (Angew. Chem. Int. Ed. Engl. Vol. 25, (1986), p239). However, further one more step is necessary in order to obtain the sulfur-containing organosilicon compounds of the present invention, and the process is not economical.

$$(R^1\text{—O})_3\text{—Si—}R^2\text{—SH} \quad \text{[V]}$$

($R^1$ is a lower alkyl group, a lower alkoxy group, a lower cycloalkoxy group, an aryloxy group, etc., and $R^2$ is a lower alkylene group)

Next, prior arts of processes for producing alkali polysulfides used as raw materials of sulfur-containing organosilicon compounds [IV] are described.

As mentioned above, since the alkali polysulfides have high water absorption properties, it is not easy to obtain anhydrides thereof.

Much energy is required in order to obtain anhydrous sulfides from hydrates of sulfides. In addition, since alkali polysulfides such as sodium disulfide and sodium tetrasulfide are viscous liquids under drying conditions, for example, at high temperatures of 120° to 130° C., it is difficult to treat them (European Patent Publication No. 361,998 and Japanese Laid-open Patent Publication No. 228588/1995).

As another method of obtaining sodium sulfide, there is a process wherein sodium alkoxide is allowed to react with hydrogen sulfide (U.S. Pat. No. 5,466,848 and Japanese Laid-open Patent Publication No. 228588/1995). Good anhydrous sulfide is obtained by this process. On the other hand, since hydrogen sulfide is toxic, it is necessary to treat it carefully, and an extra step is required in order to avoid poisoning.

Furthermore, Inorganic and Theoretical Chemistry, Vol. 2, p981 discloses a process wherein metallic sodium is allowed to react with sulfur in liquid ammonia or xylene. However, the reaction using liquid ammonia is carried out at ultra-low temperatures, and treatment of ammonia is also troublesome. Since the reaction in an aromatic solvent such as xylene proceeds explosively at about 98° C., which is a melting point of the metallic sodium, the reaction is not practical.

SUMMARY OF THE INVENTION

An object of the present invention is to provide a method of obtaining high-purity sulfur-containing organosilicon compounds having polysulfide structure in a simple manner without treatment at high temperatures or in a vacuum in view of the above-mentioned problems of the prior arts.

Another object of the present invention is to provide a method of obtaining anhydrous alkali sulfides which are useful as synthetic intermediates of the above-mentioned sulfur-containing organosilicon compounds, in a simple and safe manner without treatment at ultra-low temperatures, high temperatures or high pressure in view of the above-mentioned problems of the prior arts.

As a result of studies to achieve the above-mentioned objects, the inventors found the following two processes for producing sulfur-containing organosilicon compounds and completed the present invention.

A first process for producing the sulfur-containing organosilicon compounds according to the present invention comprises reacting sulfur, an alkali metal and halogenoalkoxysilane represented by the general formula [I]

(wherein $R^1$ is a monovalent hydrocarbon group having 1 to 5 carbon atoms, $R^2$ is a divalent hydrocarbon group having 1 to 9 carbon atoms, and X is a halogen atom), with each other, to give sulfur-containing silicon compounds represented by the general formula [II]

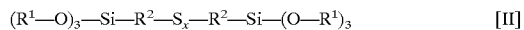

(wherein $R^1$ and $R^2$ have the same definitions as in the general formula [I], and x is an integral number of 1 to 8).

A second process for producing the sulfur-containing organosilicon compounds according to the present invention comprises reacting sulfur with an alkali metal in the presence of an aprotic solvent, and then reacting the resulting reaction product with the above-mentioned halogenoalkoxysilane [I] to give the above-mentioned sulfur-containing organosilicon compounds [II].

DETAILED DESCRIPTION OF THE INVENTION

In the first and second processes, sulfur, which is one of the starting materials, is preferably anhydrous and preferably takes the form of powder or flake for high solubility in the solvent used. The smaller the particle diameter of sulfur having such a form, the higher does sulfur exhibit reaction efficiency. It is preferable to select sulfur having appropriate particle diameter with respect to the solvent used in order to control the reaction. Since the reaction is exothermic, sulfur having large particle diameter is sometimes preferable. An amount of sulfur to be used varies with sulfur content in the intended sulfur-containing organosilicon compound [II]. For example, when a disulfide organosilicon compound is intended to be obtained, about equimolar amounts of sulfur, the alkali metal and the halogenoalkoxysilane [I] are used. When a tetrasulfide organosilicon compound is intended to be obtained, sulfur is used in an amount of about twice the amounts of the alkali metal and the halogenoalkoxysilane [I].

The alkali metal, which is another starting material, is metallic sodium, metallic potassium or metallic lithium, and preferably metallic sodium. An amount of the alkali metal to be used can be about equal to that of the halogenoalkoxysilane [I].

In the halogenoalkoxysilane [I] represented by the general formula [I],

which is the other starting material, each $R^1$ is, the same or different, a straight or branched monovalent hydrocarbon group having 1 to 5 carbon atoms, preferably a methyl group, an ethyl group or combination thereof However, $R^1$ is not limited to them. $R^2$ is a straight or branched divalent hydrocarbon group having 1 to 9 carbon atoms, preferably —$CH^2$—, —$CH_2CH_2$—, $CH_2CH_2CH_2$—, $CH_2CH_2$—Ph—$CH_2$—(Ph is a phenylene group,) or the like. X is a halogen atom exemplified by chlorine, bromine, iodine, etc.

In the first and second processes, since both the halogenoalkoxysilane [I], which is a starting material, and the sulfur-containing organosilicon compound [II], which is an object substance, are reactive with moisture, it is preferable to carry out the reaction under an inert gas atmosphere such as a nitrogen gas or argon gas atmosphere dried sufficiently.

In the first process, sulfur can be mixed with the alkali metal and the halogenoalkoxysilane [I], and they can be allowed to react under prescribed conditions. Though reaction modes can differ a little according to the order of adding these three components, the sulfur-containing organosilicon compound [II] having high purity is finally obtained with ease. For example, it is also preferable to disperse sulfur into the halogenoalkoxysilane [I], then to add the alkali metal to the obtained dispersion and to allow them to react with each other under prescribed conditions.

The first process proceeds in the absence of the solvent, but the process can be allowed to proceed in the presence of the aprotic solvent because of removal of reaction heat and smooth stirring.

The aprotic solvent can be a solvent which does not have an active hydrogen atom which reacts with the alkali metal, and it is preferable to use a solvent dried to the utmost in order to prevent hydrolysis of alkoxide due to water. Examples of the aprotic solvent which can suitably be used are aromatic hydrocarbons such as benzene, toluene and xylene, and ether solvents such as tetrahydrofuran (abbreviated as THF), tetrahydropyran, dioxane and dibutyl ether. In particular, among these ethers, using a solvent which solvates the starting material or the object substance, the reaction is promoted. In this case, when crown ether or the like is further added to the solvent as a reaction accelerator, the reaction is much more promoted.

The second process comprises a former step wherein sulfur is allowed to react with the alkali metal in the aprotic solvent, and a latter step wherein the above-mentioned halogenoalkoxysilane [I] is then added to the resulting reaction product and they are allowed to react with each other under prescribed conditions.

The preferred aprotic solvent in the second process is a solvent which can solvate an alkali metal ion or dissolve alkali sulfide. The solvent which can solvate the alkali metal ion is a solvent which can solvate the alkali metal ion by formation of chelate with the ion. The reaction of sulfur with the alkali metal is promoted by using the solvent.

The solvents which can dissolve the alkali sulfide in the present specification can be not only the solvents which can always and perfectly dissolve the alkali sulfide which forms in the reaction system by the process for production, but also the solvents can dissolve the alkali sulfide deposited in the reaction system in the solvent successively and promptly under the reaction condition. So far as the solvents can dissolve the alkali sulfide of necessary and sufficient amount required for the progress of the reaction, the alkali sulfide can deposit in the reaction system.

Examples of such a solvent are THF, 2-methyltetrahydrofuran, tetrahydropyran, crown ether, and alkyl ethers of polyhydroxy alcohols such as dimethoxyethane (DME, ethylene glycol dimethyl ether), diethylene glycol dimethyl ether, triethylene glycol dimethyl ether, diethylene glycol dibutyl ether and propylene glycol dimethyl ether. It is preferable to use a solvent dried to the utmost in order to prevent hydrolysis of alkoxide due to water. In general, a low boiling point solvent requires less energy to be recovered. However, it is particularly preferable to use THF, dimethoxyethane, etc. as the solvent since a reaction temperature of the latter step by the halogenoalkoxysilane [I] is usually 60° to 100° C.

The anhydrous alkali sulfide which is the reaction product obtained by the reaction of sulfur and the alkali metal in the aprotic solvent in the former step of the second process can be taken out of the reaction liquid and used in the latter step, or the reaction liquid containing it can be used in the latter step as it is.

The alkali sulfide which is the reaction product in the former step, that is, the synthetic intermediate in the second process is represented by the general formula (AIM)mSn (wherein AIM is an alkali metal, S is a sulfer atom, m is an integral number of 2 or 4, and n is an integral number of 1 to 9). However, some of the substance formed actually has composition distribution in a certain range. Examples of the alkali sulfide are sodium sulfide ($Na_2S$), sodium disulfide ($Na_2S_2$), sodium trisulfide ($Na_2S_3$), sodium tetrasulfide ($Na_2S_4$), lithium sulfide ($Li_2S$), lithium disulfide ($Li_2S_2$), lithium tetrasulfide ($Li_2S_4$), potassium sulfide ($K_2S$), potassium trisulfide ($K_2S_3$), potassium pentasulfide ($K_2S_5$), potassium hexasulfide ($K_2S_6$), etc.

When an alkyl ether of polyhydroxy alcohol polymer having high boiling point is used as reaction solvent, the ether can be blended with rubber together with sulfur-containing organosilicon compound [II] without separating the ether. Since the alkyl ether of polyhydroxy alcohol polymer acts as a dispersibility improver in silica blending with the rubber and a protectant of hydroxyl groups of silica, such blending is sometimes preferable.

DESCRIPTION OF THE PREFERRED EMBODIMENT

The present process is specifically described hereinafter by giving examples of the present invention. Unless the present invention deviates from the spirit thereof, the present invention is not limited to these examples.

EXAMPLE 1 a) A three-necked flask (200 ml) equipped with a condenser, a thermometer and a stirrer was first charged with 48.2 g, (0.2 mol) of triethoxysilylpropyl chloride (TESPC) and 6.4 g (0.2 mol) of powdered sulfur of 200 mesh while making dried nitrogen gas flow and then charged with 4.6 g (0.2 mol) of metallic sodium at room temperature. Then, the whole was heated at 70° C. to carry out a reaction with stirring for 24 hours.

b) After the reaction was completed, the reaction mixture was diluted with 50 ml of xylene, the resulting sodium chloride was filtered out of the reaction mixture to give a brown liquid, and the liquid was decolorized with active carbon to give a pale yellow liquid. The remaining xylene in the pale yellow liquid was removed under reduced pressure to give triethoxypropylsilyl disulfide (TEPSDS) as a reaction product.

c) The residue of TESPC, which is a starting material, in TEPSDS, which is the reaction product, was measured by gas chromatography to determine a yield (yield: 95.4%). Values of elemental analysis of the obtained reaction product are shown in Table 1.

EXAMPLE 2

A flask was charged with 60 ml of dimethoxyethane (DME, water content: 1 ppm or lower) treated with molecular sieve as an aprotic solvent. The same procedure as in Example 1 was repeated except that the amount of sulfur to be used was altered into 12.8 g (0.4 mol), the reaction condition was altered into 80° C. and five hours, and a reaction mixture was not diluted with xylene, to give triethoxypropylsilyl tetrasulfide (TEPSTS) as a reaction product (yield: 98.3%).

EXAMPLE 3

In the step a), the same three-necked flask (200 ml) as used in Example 1 was first charged with 60 ml of the same treated DME as used in Example 2 as an aprotic solvent while making dried nitrogen gas flow. To DME was added 6.4 g (0.2 mol) of powdered sulfur of 200 mesh, and then 4.6 g (0.2 mol) of metallic sodium was introduced into the flask at room temperature. Raising the temperature of the mixed liquid to about 65° C., a reaction of metallic sodium with sulfur began, and the mixed liquid became a uniform solution in about 15 minutes. Stirring was further continued at 70° C. for 45 minutes to form anhydrous sodium sulfide.

Then, 48.2 g (0.2 mol) of TESPC was added dropwise to the liquid containing anhydrous sodium sulfide for 10 minutes, the temperature of the liquid was raised to 85° C. (boiling point of DME), and the liquid was further stirred under reflux for three hours.

The same procedure as in Example 2 was repeated after the filtration step to give TEPSDS (yield: 92.3%).

EXAMPLE 4

The same procedure as in Example 3 was repeated except that the amount of sulfur to be added was altered into 12.8 g (0.4 mol) and the reaction time after adding TESPC was altered into five hours to give TEPSTS (yield: 96.9%).

COMPARATIVE EXAMPLE 1

Commercially available sodium sulfide pentahydrate (manufactured by Sankyo Chemical Co., Ltd.) was spread evenly on a pad, dried under reduced pressure of 20 mmHg at 90° C. for one hour, and further at 120° C. for three hours.

Then, the same three-necked flask (200 ml) as used in Example 1 was charged with 7.8 g (0.1 mol) of the dried sodium sulfide, 9.6 g (0.3 mol) of sulfur and 60 ml of ethanol while making dried nitrogen gas flow. Further, 48.2 g (0.2 mol) of TESPC was added dropwise thereto for 10 minutes, and a reaction was carried out for five minutes under reflux of ethanol (80° C.). After the resulting sodium chloride was filtered out, the precipitate which was considered to be a condensate of TESPC or TEPSTS was separated from the reaction mixture. Ethanol was evaporated under reduced pressure from the remaining liquid phase to give TEPSTS (34.2 g). It corresponded to 64% of the theoretical yield.

EXAMPLE 5

The same three-necked flask (200 ml) as used in Example 1 was first charged with 60 ml of the same treated DME as used in Example 2 as an aprotic solvent while making dried nitrogen gas flow, and charged with 3.2 g (0.1 mol) of powdered sulfur of 200 mesh and then 4.6 g (0.2 mol) of metallic sodium at room temperature. Raising the temperature of the mixture to about 65° C., a reaction of metallic sodium with sulfur began. After 15 minutes, the mixed liquid became a uniform solution. The reaction temperature was further kept at 70° C., and the solution was heated while stirring it for 45 minutes. DME was evaporated under reduced pressure to give sodium sulfide.

EXAMPLE 6

The same procedure as in Example 5 was repeated except that the aprotic solvent was altered into 60 ml of THF and the amount of sulfur to be used was altered into 12.8 g (0.4 mol). In this case, a reaction of metallic sodium with sulfur began at about 55° C. After 15 minutes, the mixed liquid became a uniform solution. The solution was further heated while stirring it under reflux of THF (67° C.) for 45 minutes in the same manner as in Example 5. THF was evaporated to give sodium tetrasulfide.

TABLE 1

(Elemental analysis)

|  | C % | H % | S % | Ash content % |
|---|---|---|---|---|
| TEPSDS Theoretical value | 45.5 | 8.9 | 13.5 | 25.3 |
| Example 1 Found value | 42.1 | 8.6 | 13.0 | 23.5 |
| Example 3 Found value | 44.6 | 9.0 | 12.1 | 23.0 |
| TESPTS Theoretical value | 40.1 | 7.9 | 23.8 | 22.3 |
| Example 2 Found value | 39.3 | 8.0 | 22.0 | 22.9 |
| Example 4 Found value | 40.0 | 8.2 | 22.1 | 22.2 |
| Comparative Example 1 Found value | 39.2 | 8.0 | 23.4 | 22.1 |

EVALUATION TEST

To styrene-butadiene rubber (SBR) were added TEPSDS or TEPSTS obtained in the above-mentioned Examples and Comparative Example and TEPSTS ("Commercial product" in Table 2) manufactured by Degusa Co., Ltd., respectively, and characteristics of each sulfur-containing organosilicon compound were evaluated. Similar evaluation tests were carried out for the SBR recipe wherein no sulfur-containing organosilicon compound was added at all ("No addition" in Table 2).

The recipe wherein the sulfur-containing organosilicon compound was added is as follows.

| SBR #1502 | 100 phr |
|---|---|
| Silica: Nipsil VN-3 | 40 phr |
| Softening agent: CIRCO light Sunoil | 10 phr |
| Stearic acid | 1 phr |
| Zinc oxide | 4 phr |
| Anti-oxidant dihydroquinoline system Nocrac 224 | 1 phr |
| Sulfur-containing organosilicon compound | 4 phr |

The recipe was mixing for 15 minutes by an eight-inch two-roll mill at 90° C. After the mixed product was stocked at room temperature for two days, to the mixture were added 2.75 phr of sulfur, 1.5 phr of diberzomercaptothiazole and 1.2 phr of diphenylguanidine, as a valcanization acceterators, and the whole was stocked at room temperature for a night.

Evaluation tests of the obtained compositions were carried out with respect to the following items.

1. Mooney Scorch Test

The tests were carried out at 125° C. by using a large rotor according to JIS-K6300.

2. Tensile Test and Compression Set Test

The tests were carried out according to JIS-K6301 respectively. Compression set tests were carried out at 70° C. for 70 hours under a heat treatment condition.

3. Alkali Resistance Test

A glass sample tube (10 ml) was charged with 5 ml of a 1 N aqueous NaOH solution, and a sample of 20×6×2 mm was immersed in the solution at 70° C. for 70 hours. After the sample was taken out, weight and volume changes thereof were measured.

The obtained results of evaluation are summarized in Table 2.

TABLE 2

(Evaluation results)

|  | Example 1 | Example 3 | Example 2 | Example 4 | Comparative Example 1 | Commercial product | No addition |
|---|---|---|---|---|---|---|---|
| Mooney scorch test |  |  |  |  |  |  |  |
| Minimal value | 37.6 | 36.9 | 40.1 | 39.6 | 40.8 | 41.2 | 70.6 |
| t 5 | 12.7 | 12.3 | 11.3 | 11.3 | 9.5 | 9.4 | 19.5 |
| Tensile properties 150° C. × 20 min. cured |  |  |  |  |  |  |  |
| Mo100% Mpa | 2.9 | 2.7 | 2.8 | 3.1 | 3.3 | 3.2 | 1.6 |
| Mo300% Mpa | 11.6 | 11.1 | 11.5 | 12.8 | 14.6 | 13.8 | 4.4 |
| Tensile strength Mpa | 23.5 | 21.5 | 21.7 | 21.2 | 21.4 | 21.3 | 25.7 |
| Stretch % | 465 | 460 | 450 | 425 | 380 | 400 | 760 |
| Hardness JIS-A | 68 | 68 | 71 | 71 | 70 | 70 | 65 |
| Alkali resistance 150° C. × 20 min. cured |  |  |  |  |  |  |  |
| Weight change % | −0.4 | −1.5 | −1.5 | −0.8 | −0.5 | −0.5 | −9.7 |
| Volume change % | 1.7 | 1.2 | 1.0 | 0.4 | 0.4 | 0.5 | −0.8 |
| Compression set % 150° C. × 25 min. cured | 24 | 25 | 23 | 23 | 23 | 23 | 34 |

As apparent from Table 2, the rubber containing the sulfur-containing organosilicon compound obtained in Examples has long scorch time (t5), is excellent in processing safety, and has a sufficient crosslinking rate, judging from the characteristics such as the tensile characteristics and the compression set. In addition, the sulfur-containing organosilicon compounds obtained in Examples are found to react with the rubber and silica sufficiently and to prevent the elution of silica, from the result of alkali resistance, which is a characteristic showing reactivity of the rubber and silica, and the loss in weight is a characteristic showing elution of silica, etc.

What is claimed is:

1. A process for producing a sulfur-containing organosilicon compound comprising reacting sulfur, an alkali metal and halogenoalkoxysilane represented by the general formula [I]

$$(R^1-O)_3-Si-R^2-X \qquad [I]$$

(wherein $R^1$ is a monovalent hydrocarbon group having 1 to 5 carbon atoms, $R^2$ is a divalent hydrocarbon group having 1 to 9 carbon atoms, and X is a halogen atom), with each other in the absence of a solvent, or in the presence of an aprotic solvent, to give a sulfur-containing silicon compound represented by the general formula [II]

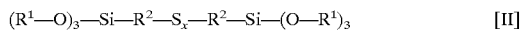

$$(R^1-O)_3-Si-R^2-S_x-R^2-Si-(O-R^1)_3 \qquad [II]$$

(wherein $R^1$ and $R^2$ have the same definitions as in the general formula [I], and x is an integral number of 1 to 8).

2. A process for producing a sulfur-containing organosilicon compound as claimed in claim 1, wherein sulfur is dispersed into the halogenoalkoxysilane [I], then an alkali metal is added to the obtained dispersion, and they are reacted with each other.

3. A process for producing a sulfur-containing organosilicon compound as claimed in claim 1, wherein the reaction is carried out in the presence of an aprotic solvent.

4. A process for producing a sulfur-containing organosilicon compound as claimed in claim 3, wherein the aprotic solvent is an aromatic hydrocarbon or an ether.

5. A process for producing a sulfur-containing organosilicon compound comprising reacting sulfur with an alkali metal in the presence of an aprotic solvent, and then reacting the resulting reaction product with halogenoalkoxysilane represented by the general formula [I]

$$(R^1-O)_3-Si-R^2-X \qquad [I]$$

(wherein $R^1$ is a monovalent hydrocarbon group having 1 to 5 carbon atoms, $R^2$ is a divalent hydrocarbon group having 1 to 9 carbon atoms, and X is a halogen atom)

to give a sulfur-containing silicon compound represented by the general formula [II]

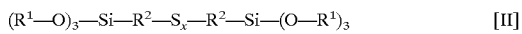

$$(R^1-O)_3-Si-R^2-S_x-R^2-Si-(O-R^1)_3 \qquad [II]$$

(wherein $R^1$ and $R^2$ have the same definitions as in the general formula [I], and x is an integral number of 1 to 8).

6. A process for producing a sulfur-containing organosilicon compound as claimed in claim 5, wherein the aprotic solvent is a solvent which can solvate an alkali metal ion or a solvent which can dissolve an alkali sulfide formed as said reaction product.

7. A process for producing a sulfur-containing organosilicon compound as claimed in claim 6, wherein the aprotic solvent is a solvent selected from the group consisting of THF, 2-methyltetrahydrofuran, tetrahydropyran, crown ether, dimethoxyethane, diethylene glycol dimethyl ether, triethylene glycol dimethyl ether, diethylene glycol dibutyl ether, propylene glycol dimethyl ether and mixtures thereof.

8. A process for producing a sulfur-containing organosilicon compound as claimed in claim 5, wherein the reaction is carried out under an inert gas atmosphere.

9. A process for producing a sulfur-containing organosilicon compound as claimed in claim 5, wherein the alkali metal is metallic sodium, metallic potassium or metallic lithium.

10. A process for producing an anhydrous alkali sulfide comprising reacting sulfur with an alkali metal in an aprotic solvent.

11. A process for producing an anhydrous alkali sulfide as claimed in claim 10, wherein the aprotic solvent is a solvent which can solvate an alkali metal ion or a solvent which can dissolve the alkali sulfide which is a reaction product.

12. A process for producing an anhydrous alkali sulfide as claimed in claim 11, wherein the aprotic solvent is a solvent selected from the group consisting of THF, 2-methyltetrahydrofuran, tetrahydropyran, crown ether, dimethoxyethane, diethylene glycol dimethyl ether, triethylene glycol dimethyl ether, diethylene glycol dibutyl ether, propylene glycol dimethyl ether and mixtures thereof.

13. A process for producing a sulfur-containing organosilicon compound as claimed in claim 1, wherein the reaction is carried out under an inert gas atmosphere.

14. A process for producing a sulfur-containing organosilicon compound as claimed in claim 1, wherein the alkali metal is metallic sodium, metallic potassium or metallic lithium.

15. A process for producing a sulfur-containing organosilicon compound as claimed in claim 2, wherein the reaction is carried out in the presence of an aprotic solvent.

* * * * *